(12) United States Patent
Silverman et al.

(10) Patent No.: US 10,058,097 B2
(45) Date of Patent: Aug. 28, 2018

(54) METHODS TO INCREASE CORN PRODUCTIVITY

(71) Applicant: Valent BioSciences Corporation, Libertyville, IL (US)

(72) Inventors: Franklin Paul Silverman, Highland Park, IL (US); Xiaozhong Liu, Vernon Hills, IL (US); Kimberly Ann Falco, Crystal Lake, IL (US); Derek D. Woolard, Zion, IL (US)

(73) Assignee: VALENT BIOSCIENCES CORPORATION, Libertyville, IL (US)

( * ) Notice: Subject to any disclaimer, the term of this patent is extended or adjusted under 35 U.S.C. 154(b) by 2 days.

(21) Appl. No.: 15/459,052

(22) Filed: Mar. 15, 2017

(65) Prior Publication Data
US 2017/0265467 A1    Sep. 21, 2017

Related U.S. Application Data

(60) Provisional application No. 62/308,542, filed on Mar. 15, 2016.

(51) Int. Cl.
| | |
|---|---|
| *A01N 43/12* | (2006.01) |
| *A01N 45/00* | (2006.01) |
| *A01N 37/44* | (2006.01) |
| *A01N 37/42* | (2006.01) |

(52) U.S. Cl.
CPC ............ *A01N 43/12* (2013.01); *A01N 37/42* (2013.01); *A01N 37/44* (2013.01); *A01N 45/00* (2013.01)

(58) Field of Classification Search
CPC ........ A01N 43/12; A01N 37/36; A01N 37/02; A01N 37/44; A01N 45/00; A01N 37/42
See application file for complete search history.

(56) References Cited

U.S. PATENT DOCUMENTS

2014/0213454 A1* 7/2014 Kaiser ................... A01N 45/00
                                                                  504/140

OTHER PUBLICATIONS

Hassanein, R., Improving Salt Tolerance of *Zea mays* L. Plants by Presoaking Their Grains in Glycine Betaine, 2009, Australian Journal of Basic and Applied Science, vol. 3, Issue 2, pp. 928-942.*
Miri, H.R., The interaction effect of drought and exogenous application of glycine betaine on corn (*Zea mays* L.), European Journal of Experimental Biology, 2013, vol. 3, Issue 5, pp. 197-206.*
CN102701861, Plant Nutrient Liquid Fertilizer, Oct. 3, 2012, Machine Translation from Patent Tranlate (EPO), pp. 1-16.*

* cited by examiner

*Primary Examiner* — John Pak
*Assistant Examiner* — Andriae M Holt
(74) *Attorney, Agent, or Firm* — Wood, Phillips, Katz, Clark & Mortimer

(57) ABSTRACT

The present invention is directed to compositions and methods for improving corn growth. Methods of the invention comprise applying an effective amount of a mixture consisting of a gibberellin and glycine betaine to the corn plant. The present invention is further directed to methods for improving corn growth comprising applying an effective amount of a mixture of a gibberellin, (S)-(+)-abscisic acid and glycine betaine to a corn plant.

16 Claims, No Drawings

METHODS TO INCREASE CORN PRODUCTIVITY

FIELD OF THE INVENTION

The present invention is directed to methods of increasing growth of a corn plant comprising applying an effective amount of a composition comprising a mixture of one or more gibberellins and glycine betaine to the corn plant. The present invention is further directed to methods of increasing growth in a corn plant by applying an effective amount of a composition comprising a mixture of one or more gibberellins, (S)-abscisic acid (ABA) and glycine betaine.

BACKGROUND OF THE INVENTION

Corn is one of the most widely used crops in the world. Corn is an important source of livestock feed and may be converted to ethanol for fuel and industrial applications. In an attempt to meet the growing need for grain, corn growers continually seek to improve production in order to maximize yields. However, corn plants are subjected to stress conditions that negatively affect yield such as cold temperatures, drought and nutrient shortage. Further, even under ideal conditions it is desirable to maximize corn plant yields to ensure efficient use of fields and harvesting equipment.

Plant growth regulators are one tool that corn growers can use in order to influence the growth of their plants. However, the effects of plant growth regulators vary due, in part, to the physiology and developmental stage of the plant. Additionally, mixtures of growth regulators often have a different effect on the physiology than the individual compounds.

Gibberellins are endogenous corn plant growth regulators with many roles in growth and development. For example, $GA_3$ stimulates the aleurone cells of germinating grains to produce lytic enzymes that mobilize starch reserves and stimulate the growth of the embryo, causing seed germination. Examples of effective commercially available $GA_3$ formulations include ProGibb® 40% and RyzUp SmartGrass® (both available from Valent BioSciences Corporation, ProGibb and RyzUp SmartGrass are registered trademarks of Valent BioSciences Corporation). $A_4$ is the active gibberellin in many plant species and exogenous application induces similar growth promotion to $GA_{3,V}$. Examples of effective commercially available $GA_4$ containing formulations include ProVide® and Regulex® (both available from Valent BioSciences Corporation, ProVide and Regulex are registered trademarks of Valent BioSciences Corporation). Application of $GA_3$, to vegetative phase corn has been shown to increase plant height (see Kaiser et al., International Patent Application WO 2014/120882).

Glycine betaine ("GB") (CAS No. 107-43-7) is a solute that accumulates in plants, micro-organisms and fungi in response to abiotic stress. Exogenous application of GB to plants has been shown to confer abiotic stress tolerance (Chen and Murata, 2008. Trends in Plant Sciences 13: 499-505). Specifically, GB induces resistance to chilling, freezing, and drought across multiple plant species. However, the levels of stress protection observed, although significant, are of limited commercial value. $GA_3$ is a plant growth regulator that also confers tolerance to a variety of stresses. In the studies disclosed here, GB increases both the anti-stress activity and the growth-promoting activity of gibberellins. To our knowledge this is a novel use of GB. Corn growers constantly strive to increase yield of either grain or silage due to both high demand and the costs associated with production. Accordingly, there is a need for new methods to improve the growth of corn under non-stressed and stressed conditions.

SUMMARY OF THE INVENTION

In one aspect, the present invention is directed to methods for increasing growth of a corn plant comprising applying mixtures of a gibberellins and glycine betaine to the corn plant.

In another aspect, the present invention is directed to methods for increasing growth of a corn plant comprising applying mixtures of a gibberellin, (S)-(+)-abscisic acid and glycine betaine to the corn plant.

In another aspect, the present invention is directed to compositions for increasing growth of a corn plant comprising a mixture of a gibberellin and glycine betaine, preferably the gibberellin selected from the group consisting of $GA_3$ or $GA_4$.

In another aspect, the present invention is directed to compositions for increasing growth of a corn plant comprising a mixture of one or more gibberellins, (S)-(+)-abscisic acid and glycine betaine, preferably the gibberellin are selected from the group consisting of $GA_3$ or $GA_4$.

DETAILED DESCRIPTION OF THE INVENTION

Applicant unexpectedly discovered that a mixture of gibberellin and glycine betaine ("GB") increased growth, stress resistance and yield of corn.

In one embodiment, the present invention is directed to methods for increasing growth of a corn plant comprising applying an effective amount of a mixture of a gibberellins and glycine betaine ("GB") to the corn plant.

In another embodiment, the present invention is directed to methods for increasing growth of a corn plant comprising applying an effective amount of a mixture of a gibberellin, GB and (S)-(+)-abscisic acid ("S-ABA") to the corn plant.

In another embodiment, the present invention is directed to compositions for increasing growth of a corn plant comprising a mixture of a gibberellin and GB.

In another embodiment, the present invention is directed to compositions for increasing growth of a corn plant comprising a mixture of a gibberellin, GB, and S-ABA.

Gibberellins suitable for use in the present invention include, but are not limited to, gibberellic acid ("$GA_3$") or gibberellin A4 ("$GA_4$").

In another embodiment, the present invention is directed to methods for increasing growth of a corn plant comprising applying an effective amount of a gibberellin, (5)-(+)-abscisic acid and glycine betaine to the corn plant.

In a preferred embodiment, the present invention is directed to methods for increasing growth of a corn plant comprising applying a composition comprising a mixture of about 60 to about 120 milligrams per liter of a gibberellin selected from the group consisting of $GA_3$ or $GA_4$ and about 1,000 to about 10,000 milligrams per liter of glycine betaine to the corn plant.

In the present invention, the corn plant may be inbred or hybrid. In a preferred embodiment, the corn is an inbred variety. In another embodiment, the corn plant is a hybrid variety.

In another embodiment, the corn plant is genetically modified. In a preferred embodiment, the genetically modified corn plant expresses herbicide resistance, insect resistance, drought tolerance or increased physiological function.

In another embodiment, the corn plant is subjected to abiotic stress. Abiotic stresses include, but are not limited to, cold, heat, drought, low nutrients and salinity.

In one embodiment, the corn plant is subject to cold stress following the application of a composition of the present invention. As used herein, cold stress refers to conditions of low temperature (e.g. 10° C.) wherein plant growth is significantly slowed as compared to greenhouse conditions that support optimal growth and development.

In another embodiment, the corn is subjected to nutrient stress prior to application of a composition of the present invention. As used herein, nutrient stress refers to nutrient conditions wherein plant growth is significantly slowed as compared to nutrient conditions that support optimal growth and development.

In another embodiment, the corn is subjected to drought stress following application of a composition of the present invention. As used herein, drought stress refers to a significant slowing of plant growth due to lack of adequate water as compared to water availability that is sufficient to support optimal growth and development.

In a preferred embodiment, the gibberellin and GB are applied during the corn growth stage period beginning at V2 and ending at V6. In a more preferred embodiment, the gibberellin and GB are applied during the corn growth stage period beginning at V3 and ending at V6. Applicant has referred to corn developmental stages throughout the application as "V" stages. The "V" stages are designated numerically as V1, V2, V3, etc. In this identification system of V(n), (n) represents the number of leaves with visible collars. Each leaf stage is defined according to the uppermost leaf whose leaf collar is visible (see Corn Growth and Development, 2011. Abendroth, L, Elmore, R, Boyer, M and Marlay, S, Iowa State University Press). "VT" refers to tassel emergence growth stage and is not an early vegetative stage of corn.

In another embodiment, from about 6 to about 21 grams of gibberellin per hectare are applied to the corn plant. In a preferred embodiment, from 12 to 20 grams of $GA_3$ per hectare is applied to the corn plant. In the most preferred embodiment, 16.8 grams of gibberellin per hectare are applied to the corn plant.

In yet another embodiment, from about 840 to 2,000 grams of GB per hectare are applied to the corn plant. In a more preferred embodiment, 1,000 to 1,600 grams of GB per hectare is applied to the corn plant. In the most preferred embodiment, 1,400 grams of GB per hectare is applied to the corn plant.

In a preferred embodiment, the increased growth in the corn plant results in increased corn yield.

In another embodiment, the gibberellin and GB can be applied with an herbicide such as glyphosate, mesotrione, halosulfuron, saflufenacil or dicamba.

In another embodiment, the one or more gibberellins and GB can be applied with a fungicide such as tetraconazole, metconazole, a strobilurin, or a combined strobilurin-azole product.

In another embodiment, the gibberellin and GB can be applied with an insecticide such as methylparathion, bifenthryn, esfenvalerate, lorsban, carbaryl or lannate.

In yet another embodiment, the one or more gibberellins and GB can be applied with foliar fertilizers such as CoRoN® (available from and registered trademark of Helena Chemical), a controlled-release nitrogen, or BioForge (available from Stoller USA), which is largely N,N'-diformyl urea, or other micro nutrient-containing sprays.

In another embodiment, the compositions of the present invention further comprise a non-ionic surface-active agent.

The gibberellin and GB mixture can be applied by any convenient means. Those skilled in the art are familiar with the modes of application that include foliar applications such as spraying, dusting, and granular applications; soil applications including spraying, in-furrow treatments, chemigation or side-dressing.

Aqueous spray solutions utilized in the present invention generally contain from about 0.01% to about 0.5% (v/v) of a non-ionic surface-active agent.

The surface active agent comprises at least one non-ionic surfactant. In general, the non-ionic surfactant may be any known non-ionic surfactant in the art. Suitable non-ionic surfactants are in general oligomers and polymers. Suitable polymers include alkylene oxide random and block copolymers such as ethylene oxide-propylene oxide block copolymers (EO/PO block copolymers), including both EO-PO-EO and PO-EO-PO block copolymers; ethylene oxide-butylene oxide random and block copolymers, C2-6 alkyl adducts of ethylene oxide-propylene oxide random and block copolymers, C2-6 alkyl adducts of ethylene oxide-butylene oxide random and block copolymers, polyoxyethylene-polyoxypropylene monoalkylethers, such as methyl ether, ethyl ether, propyl ether, butyl ether or mixtures thereof; vinylacetate/vinylpyrrolidone copolymers; alkylated vinylpyrrolidone copolymers; polyvinylpyrrolidone; and polyalkyleneglycol, including the polypropylene glycols and polyethylene glycols. Other non-ionic agents are the lecithins; and silicone surface active agents (water soluble or dispersible surface active agents having a skeleton which comprises a siloxane chain e.g. Silwet L77®; Silwet L77 is a registered trademark of Momentive Performance Materials Inc. A suitable mixture in mineral oil is ATPLUS® 411 F (ATPLUS is a registered trademark of Uniqema Americas LLC.)

As used herein, "effective amount" refers to the amount of the $GA_x$ and/or glycine betaine that will increase growth, improve drought stress tolerance, improve chilling stress tolerance, and/or improve yield. The "effective amount" will vary depending on the gibberellin and glycine betaine concentration, application volume, the corn variety being treated, the severity of the stress, the result desired, and the life stage of the plants, among other factors. Thus, it is not always possible to specify an exact "effective amount." However, an appropriate "effective amount" in any individual case may be determined by one of ordinary skill in the art.

As used herein, "improving" means that the corn has more of the specific quality than the corn would have had it if it had not been treated by methods of the present invention.

The disclosed embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The following examples are intended to illustrate the present invention and to teach one of ordinary skill in the art how to use the compositions of the present invention. They are not intended to be limiting in any way.

EXAMPLES

In several of the following examples, corn was grown in greenhouse conditions, which are defined as follows. Seeds of a commercial hybrid variety were sown in Pro-Mix® BX (Pro-Mix is a registered trademark of Premier Horticulture Ltd.) with the addition of Osmocote (14-14-14) and gypsum in three-liter pots. Greenhouses were kept at 25±3° C. under a 16:8 hour photoperiod, with illumination at canopy level of ~250 µmoles $m^{-2}s^{-1}$. Corn was typically fertigated with Peters 21-5-20+micronutrients, calcium ammonium nitrate and magnesium sulfate. Typical growth rates for corn under these conditions ranged from 4-5 cm/day.

In most greenhouse studies, spray applications were made. These applications were made in a track sprayer outfitted with a 4001E Teejet® nozzle (Teejet is available from and a registered trademark of Spraying Systems Co., Glendale Heights, Ill., USA) and applied at 40 psi. Although application volumes did vary between some studies, generally, 30 gallons/acre of spray solution was applied. Following spray applications, plants were returned to the greenhouse. Typically, experiments were blocked according to plant size, and a randomized complete block design (RCB) was used.

In stress studies, plants were subjected to various stresses. In cold stress studies, after spraying, plants were grown in the greenhouse for an additional 48 hours before being measured and moved to a CMP6050 CONVIRON® chamber kept at 10° C. (Conviron is a registered trademark of Controlled Environments Limited Corporation). Illumination was at ~225 µMoles, and light:dark conditions were on a 12:12 hour photoperiod. After 120 hours of chilling, plants were removed from the cold, measured, and returned to the greenhouse for 48 hours prior to harvest.

In drought stress studies, corn plants were sprayed at the V4 stage with solutions containing a non-ionic surfactant (0.25%, v/v) at 30 gallons of spray solution/acre and growth was determined by change in height from time of treatment or fresh and dry shoot weight measurements 14 days later.

Example 1

In a greenhouse study conducted in Long Grove, Ill., corn plants were sprayed at V3 stage with solutions containing a non-ionic surfactant (0.25%, v/v) at 30 gallons of spray solution/acre and growth was followed for nine days.

TABLE 1

Growth of corn following spray application with $GA_3$ or GB.

| Treatment | Growth over 9 days (cm) | Growth Rate (cm/day) | Dry Weight/ Plant (g) |
|---|---|---|---|
| Control | 40.6 | 4.51 | 2.68 |
| $GA_3$ 120 mg/liter | 42.9 | 4.76 | 2.92 |
| GB 3000 mg/liter | 40.4 | 4.49 | 2.75 |
| $GA_3$ 120 mg/liter + GB 3000 mg/liter | 44.1 (1.65) | 4.90 (1.68) | 2.97 (0.95) | n = 7
Number in parentheses denotes the synergy factor.

As seen in Table 1, the mixtures of the present invention provided a more than additive effect (i.e. synergistic effect). Synergy was determined using the following formula, in which a synergy factor is calculated by the Abbott method:

$$\% C_{exp} = A + B - (AB/100),$$

here % $C_{exp}$ is the expected efficacy and "in which A and B are the increase in growth (or resistance to stress) levels given by the single [plant growth regulators]. If the ratio between the experimentally observed efficacy of the mixture Cobs and the expected efficacy of the mixture is greater than 1, synergistic interactions are present in the mixture" (Gisi, Synergistic Interaction of Fungicides in Mixtures, The American Phytopathological Society, 86:11, 1273-1279, 1996).

Based on a conservative approach, synergy was determined to be present at ratios of ≥1.10. When grown under non-stressed conditions, $GA_3$ growth was synergized by the addition of 3,000 mg/liter glycine betaine ("GB"), with a synergy factor of 1.65 for growth and 1.68 for growth rate while dry weight/plant was not synergistic with a synergy factor of 0.95.

In a greenhouse study, plants were sprayed at V3 stage with solutions containing a non-ionic surfactant (0.25%, v/v) at 30 gallons of spray solution/acre and growth was followed for seven days.

TABLE 2

Effect of $GA_3$ + GB dose on growth of greenhouse-grown maize.

| $GA_3$ mg/liter | GB mg/liter | Plant Growth over 7 days (cm) | Growth Rate (cm/day) |
|---|---|---|---|
| 0 | 0 | 30.80 | 4.41 |
| 120 | 0 | 34.01 | 4.86 |
| 120 | 1000 | 36.85 | 5.26 |
| 120 | 3000 | 36.85 | 5.26 |
| 120 | 5000 | 37.19 | 5.31 |
| 120 | 10,000 | 37.78 | 5.40 | n = 7 plants

In the study in Table 2, GB increased $GA_3$-induced corn growth in a dose-dependent manner. When 120 mg/liter $GA_3$ was combined with 1,000 mg/liter GB, the resulting growth increased by 8.3% over the $GA_3$ alone; with $GA_3$+10,000 mg/liter GB, growth was increased by 11.1%, as compared to $GA_3$ alone, and a 22.5% increase in growth rate over the control.

In a separate study, the effect of one rate of GB on various doses of $GA_3$ was studied. See Table 3.

TABLE 3

Effect of $GA_3$ dose +/− GB on growth of greenhouse-grown maize.

| $GA_3$ mg/liter | GB mg/liter | Plant Growth over 7 days (cm) | Growth Rate, 0-7 day(s) (cm/day(s)) | Plant Growth over 14 days (cm) | Growth Rate, 0-14 day(s) (cm/day(s)) |
|---|---|---|---|---|---|
| 0 | 0 | 16.5 | 2.36 | 43.5 | 6.21 |
| 0 | 10000 | 17.6 | 2.51 | 43.6 | 6.23 |
| 30 | 0 | 22.2 | 3.17 | 47.8 | 6.82 |
| 30 | 10000 | 23.4 (1.07) | 3.34 (1.08) | 48.1 (1.05) | 6.87 (1.05) |
| 60 | 0 | 25.0 | 3.57 | 50.7 | 7.24 |
| 60 | 10000 | 26.6 (1.12) | 3.80 (1.12) | 52.8 (1.28) | 7.55 (1.28) |
| 120 | 0 | 27.3 | 3.91 | 51.4 | 7.35 |
| 120 | 10000 | 28.7 (1.09) | 4.10 (1.09) | 54.4 (1.37) | 7.77 (1.35) |
| 240 | 0 | 29.8 | 4.25 | 55.6 | 7.94 |
| 240 | 10000 | 30.3 (1.02) | 4.33 (1.03) | 56.3 (1.05) | 8.04 (1.05) | n = 8 plants
Number in parentheses denotes the synergy factor.

The data in Table 3 demonstrates that GB can increase the effects of $GA_3$, regardless of $GA_3$ rate. In addition to increasing the effectiveness of the $GA_3$-induced growth at seven days, it also increases the time that $GA_3$ induces growth. For example, at 60 mg/liter $GA_3$, the addition of GB increased the growth rate at 7 days after spraying by 6.3%; at 14 days after spraying, the 60 mg/liter $GA_3$+GB grew faster than the 120 mg/liter $GA_3$-treated plants. At 14 days, the rates of growth were synergistic at 60 mg/liter (synergy factor 1.28) and 120 mg/liter (synergy factor of 1.37) $GA_3$+GB.

In the same study, leaf chlorophyll was monitored by measurements with a SPAD meter (Minolta Model 502; Ramsey, N.J.). In this study, the chlorophyll level in the most recently fully-expanded leaf was measured at five different points and the results averaged. These data are shown in Table 4.

TABLE 4

Effect of $GA_3$ dose +/− GB on chlorophyll of greenhouse-grown maize.

| $GA_3$ mg/liter | GB mg/liter | Chlorophyll (SPAD reading) 14 days |
|---|---|---|
| 0 | 0 | 34.3 |
| 0 | 10000 | 34.0 |
| 30 | 0 | 33.1 |
| 30 | 10000 | 34.3 |
| 60 | 0 | 32.9 |
| 60 | 10000 | 33.3 |
| 120 | 0 | 31.6 |
| 120 | 10000 | 32.9 |
| 240 | 0 | 31.1 |
| 240 | 10000 | 32.6 | n = 8 plants

As is shown in Table 4, one effect of $GA_3$ application to corn is to reduce greenness, as indicated by SPAD chlorophyll. This is likely due to a dilution effect of endogenous chlorophyll due to greater leaf surface area. The addition of 10,000 mg/liter GB to corn treated with $GA_3$ results in an increase in greenness (leaf chlorophyll content), as compared to corn treated with $GA_3$ alone. This result may make the treated plants better able to exploit the $GA_3$-induced increase in surface area, by increasing photosynthetic pigment (i.e. chlorophyll).

Example 2

In a greenhouse study, the effect of combining GB with $GA_4$ was studied.

TABLE 5

Growth of corn following spray application with GB alone or in combination with $GA_4$ for nine days.

| Treatment | Plant Growth over 9 days (cm) | Growth Rate (cm/day) | Dry Weight (g) |
|---|---|---|---|
| Control | 53.9 | 6.0 | 6.67 |
| GB, 10,000 mg/liter | 55.2 | 6.1 | 7.47 |
| $GA_4$, 120 mg/liter | 64.1 | 7.1 | 7.68 |
| $GA_4$ 120 mg/liter + GB, 10,000 mg/liter | 69.3 (1.37) | 7.7 (1.44) | 7.39 (0.43) | n = 7 plants
Number in parentheses denotes the synergy factor.

In Table 5, GB was able to synergize both corn plant growth and growth rates when used in combination with $GA_4$. In combination with $GA_4$, GB synergized corn growth and growth rates with synergy factors of 1.37 and 1.42, respectively. These results demonstrate that the GB-mediated increases in gibberellin-induced growth of corn are not limited to $GA_3$.

When gibberellins are combined with specific ratios of (S)-(+)-abscisic acid ("(S)-ABA"), a surprising enhancement of corn growth after application is often observed. The addition of GB to gibberellin+(S)-ABA spray combinations further increases the growth-promoting activity of the mixtures, as is shown in Table 6.

TABLE 6

Greenhouse study examining the effects of Gibberellins, (S)-ABA and Glycine betaine on corn growth.

| Treatment | 7 days Change in Height (cm) | 14 days Change in Height (cm) | Dry Weight (g) |
|---|---|---|---|
| Control | 31.2 | 60.6 | 7.3 |
| $GA_3$ 120 mg/liter | 32.5 | 62.8 | 8.1 |
| $GA_3$ 120 mg/liter + GB 10000 mg/liter | 34.7 | 64.9 | 7.0 |
| $GA_3$ 120 mg/liter + (S)-ABA 8.8 mg/liter | 34.1 | 62.4 | 8.1 |
| $GA_3$ + (S)-ABA + GB | 34.4 | 64.3 | 7.0 |
| $GA_4$ 120 mg/liter | 33.9 | 62.2 | 8.1 |
| $GA_4$ 120 mg/liter + GB 10000 mg/liter | 36.4 | 64.6 | 7.8 |
| $GA_4$ 120 mg/liter + (S)-ABA 8.8 mg/liter | 33.7 | 64.0 | 7.5 |
| $GA_4$ + (S)-ABA + GB | 40.2 | 67.5 | 7.7 |

Although all treatments numerically increased corn height, all combinations that included GB (10,000 mg/liter) provided a significant height increase compared to the control at both 7 and 14 days after treatment. At 7 days post-treatment, $GA_3$+(S)-ABA and $GA_4$+(S)-ABA combinations increased plant height by 9.3% and 8.0%, respectively, when compared to the control. Surprisingly, the addition of GB to both $GA_3$+(S)-ABA and $GA_4$+(S)-ABA combinations enhanced growth 7 days after treatment by an additional 1.0% and 20.8%, respectively. This additional growth enhancement trend persisted through 14 days after treatment. While treatments containing the $GA_3$+GB combination did not produce an increase in shoot dry weight, treatments that contained the $GA_4$+GB combination did provide a substantial increase in shoot dry weight when compared to the control. Specifically, $GA_4$+GB increased shoot dry weight from 5.5 to 6.8% over that of the control.

Example 3

Abiotic stresses of plants include, but are not limited to, cold, drought, heat, nutrients, and salinity. Early in the season in the Midwestern United States, corn is frequently exposed to cold temperatures and nutrient limitation. The addition of GB to $GA_3$ increased the positive aspects of $GA_3$ mitigation of abiotic stress.

In a greenhouse and growth room study conducted in Long Grove, Ill., corn plants of a commonly grown hybrid were subjected to the following stress regimen: at two days post-foliar application, plants were moved into a controlled environment chamber, where the temperature was maintained at 10° C. with a 12:12 hour photoperiod for five days. At the end of the chilling period, the corn was moved back to the greenhouse for two days before destructive harvest.

TABLE 7

Growth of corn following spray application with GA₃ or
GB and subjected to chilling stress at 10° C. for five days.

| Treatment | Growth over 9 days (cm) | Growth Rate (cm/day) | Leaf Area of L1-L5 (cm²) |
|---|---|---|---|
| Control | 20.11 | 2.23 | 349.25 |
| GA₃ 120 mg/liter | 21.43 | 2.38 | 324.24 |
| GB 3000 mg/liter | 19.41 | 2.16 | 356.47 |
| GA₃ 120 mg/liter + GB 3000 mg/liter | 24.77 (7.0) | 2.75 (6.14) | 362.67 (−0.78) | n = 7 plants
Number in parentheses denotes the synergy factor.

Although GB did not increase growth alone, it synergized GA₃-induced corn growth (synergy factor 7.0) in a cold stress study, which included five days at 10° C. (Table 7). Interestingly, GB increased leaf area alone and in combination with GA₃, whereas GA₃ alone did not. Increasing leaf area, particularly under cool conditions, allows the plant to increase its capture of sunlight for photosynthesis, and sets up the plant for better growth when conditions are more favorable. These results demonstrate that GB may increase the positive effects of GA₃ on corn under cold stress.

During rainy periods in March-May in the Midwestern United States, nitrogen fertilizer for corn is often limited due to a combination of leaching and mineralization. GB included with GA₃ can help overcome the slow growth caused by low nutrients. In a greenhouse study in Long Grove, Ill. we evaluated the effect of GA₃, GB and the combination under 'normal nutrient' and limited nutrient conditions. These results are shown in Table 8.

TABLE 8

Growth of corn following spray application with GA₃ and/or GB for 7 days
and subjected to nutrient stress during growth and after spraying.

| Treatment | Change in Height (cm) | | Leaf Area (L1-L6) (cm²) | | Dry Weight (g) | |
|---|---|---|---|---|---|---|
| | Low Nutrients | Normal Nutrients | Low Nutrients | Normal Nutrients | Low Nutrients | Normal Nutrients |
| Control | 27.87 | 34.44 | 592.40 | 658.68 | 2.55 | 3.11 |
| GA₃ 120 mg/liter | 30.34 | 38.83 | 588.66 | 629.45 | 2.50 | 2.86 |
| GB 10,000 mg/liter | 24.54 | 35.37 | 611.73 | 656.76 | 2.79 | 3.25 |
| GA₃ 120 mg/liter + GB 10,000 mg/liter | 31.77 | 40.29 (1.12) | 591.12 | 653.57 | 2.64 | 3.18 | n = 7 plants
Number in parentheses denotes the synergy factor.

In Table 8, combining GA₃ with GB provided benefits under low nutrient conditions. The combination of GB with GA₃ increased height under low nutrient conditions and was synergistic under high nutrient conditions (synergy factor=1.12). GA₃ alone caused reductions in leaf area and dry weight, regardless of nutrient status. The combination of GB and GA₃ increased leaf area to those seen in the controls and numerically increased dry weight over those observed in the controls.

In greenhouse drought stress studies, corn plants were treated and subsequently watered with an automated irrigation system that maintained the soil moisture in the pots at 45% or 20% volumetric water content ("VWC"). Plants set to 20% after treatment took about 4 days without the automated system adding water to those pots to reach 20% VWC and then the automated system added water as needed to maintain 20% VWC. Total soil moisture capacity was 45% VWC and 20% VWC represented drought stress conditions. This would be considered chronic stress, as a lower level of VWC was maintained throughout the experiment after treatment.

TABLE 9

Growth of potted corn plants following spray application with
Gibberellic Acid (GA₃) and/or GB for 14 days and subjected
to drought stress after spraying.

| Treatment | Pot Soil Moisture, Percent Volumetric Water Content | Percent Fresh Weight of Drought Stressed Control | Percent Dry Weight of Drought Stressed Control |
|---|---|---|---|
| 0.25% (v/v) Nonionic surfactant in water | 45 | 159.97 | 153.27 |
| 0.25% (v/v) Nonionic surfactant in water | 20 | 100.00 | 100.00 |
| 120 mg/liter Gibberelli Acid (GA₃) | 20 | 106.11 | 103.32 |
| 3000 mg/liter Glycine betaine (GB) | 20 | 93.16 | 94.33 |
| 120 mg/liter GA₃ + 3000 mg/liter GB | 20 | 121.11 | 120.60 | n = 5;
Percent VWC is equal to the volumetric water content of the soil. In our medium, 45% VWC is at capacity; 20% VWC is considered drought-stressed.

In Table 9, control plants sprayed with non-ionic surfactant solution (0.25% (v/v) only and held at 45% VWC after treatment grew much more than plants sprayed with surfactant solution and then held at 20% soil moisture (chronic drought). Spraying plants with GA₃ increased shoot growth under drought conditions compared to plants sprayed with surfactant alone. Spraying potted corn plants with glycine betaine decreased the growth of the plants under drought conditions. Spraying corn with a combination of GA₃ and GB provided additional shoot growth under low soil moisture conditions over that observed with GA₃ alone.

In a separate acute drought stress greenhouse study conducted in Long Grove, Ill., corn plants were sprayed at V4 stage with solutions containing a non-ionic surfactant (0.25%, v/v) at 30 gallons of spray solution/acre and growth was determined by shoot height increase 7 and 14 days later. After treatment corn plants were not watered with the exception of one treatment of control (aqueous surfactant solution) that were watered as needed (well-watered control).

TABLE 10

Growth of potted corn plants following spray application with gibberellic acid (GA₃) and/or glycine betaine (GB) for 7 and 14 days and subjected to acute drought stress after spraying.

| Treatment | Shoot Growth 7 days after treatment as Percent Increase as compared to Drought Stressed Control | Shoot Growth 14 days after treatment as Percent Increase as compared to Drought Stressed Control |
|---|---|---|
| Treated Control (0.25% (v/v) NIS), well watered | 151.2 | 306.6 |
| Treated Control (0.25% (v/v) NIS), drought stressed | 100.0 | 100.0 |
| 120 ppm Gibberellic Acid (GA₃), drought stressed | 116.9 | 118.7 |
| 3000 ppm Glycine betaine (GB), drought stressed | 95.9 | 97.6 |
| 120 ppm GA₃ + 3000 ppm GB, drought stressed | 130.2 | 130.7 |

In Table 10, the treated control plants grew 50% more in the first 7 days than control plants subjected to acute drought. Plants treated with GA₃ showed increased growth under drought by 16.9% at 7 days and 18.7% at 14 days as compared to controls. In contrast, glycine betaine-treated plants showed slightly reduced growth under drought. Treating plants with a combination of GA₃ and GB increased shoot growth by about 30% under drought conditions. This was about 13% greater growth than that observed with GA₃ alone. Surprisingly, the combination of GB with GA₃ significantly increased shoot height when the corn was grown without irrigation in the greenhouse for two weeks after treatment.

Example 4

A field study was conducted at Woodstock, Ill. in 2014. Seeds of a central corn belt hybrid with 111 days to maturity were sown on May 20, 2014. Plants were sprayed at V4 with solutions containing a non-ionic surfactant (0.25%, v/v) at 15 gallons of spray solution/acre. Growth was followed by measuring shoot height in centimeters for 60 plants in each replicate at 7 and 14 days post spraying.

TABLE 11

Effect of spray applications of GA₃ (120 mg/liter) and GB (10,000 mg/liter) on corn growth at Woodstock, IL.

| Treatment | Height at 7 days post spray | Height at 14 days post spray | Growth Rate (cm/day) from 7-14 days |
|---|---|---|---|
| Control | 63.8 | 98.71 | 4.99 |
| GA₃ (120 mg/liter) | 68.2 | 102.4 | 4.89 |
| GA₃ (120 mg/liter) + GB (10,000 mg/liter) | 71.8 | 107.2 | 5.06 |

The data in Table 11 show that the results of GB-enhancing GA₃-induced growth of corn are not limited to the laboratory or greenhouse, but are also observed in the field. One week after treatment application, corn plants sprayed with GA₃ (120 mg/liter) exhibited 6.9% more growth than plants that were treated with the surfactant alone. At that same time, plants treated with the combination of GA₃ (120 mg/liter) and GB (10,000 mg/liter) unexpectedly exhibited an additional 5.6% increase in growth compared to plants treated with GA₃ alone, providing a 12.5% growth increase over the control plants. This same growth enhancement trend persisted through 14 days post-spraying.

A field study was conducted at Woodstock, Ill. Seeds of a central corn belt variety with 103 days to maturity were sown and plants were sprayed at V5 with solutions containing a non-ionic surfactant (0.25%, v/v) at 15 gallons of spray solution/acre. Growth was followed by measuring shoot heights in centimeters 50 plants in each replicate at 7 and 13 days post-spraying. The number of kernels per kernel-row (average kernel number) as well as the number of kernel-rows (average row number) per ear was counted for 50 plants in each replicate 7 days before harvest. The harvest grain yield was corrected to 15% moisture.

TABLE 12

Corn experiment conducted at Woodstock, IL in 2015.

| Treatment | Height at 7 days post spray (cm) | Height at 13 days post spray (cm) | Average row number per ear | Average kernel number per row | Yield (bu/acre) |
|---|---|---|---|---|---|
| Control | 61.2 | 84.4 | 16.7 | 32.99 | 217.5 |
| GA₃ (120 mg/liter) | 69.6 | 88.6 | 16.8 | 31.59 | 222.8 |
| GA₃ (120 mg/liter) + GB (10000 mg/liter) | 69.9 | 88.3 | 17.1 | 31.12 | 221.3 |
| GA₃ (120 mg/liter) + (S)-ABA (9 mg/liter) | 67.8 | 87.4 | 17.1 | 32.16 | 215.6 |
| GA₃ (120 mg/liter) + (S)-ABA (9 mg/liter) + GB (10000 mg/liter) | 68.8 | 89.4 | 16.6 | 33.25 | 219.1 |

As shown in Table 12, all treated corn plants exhibited enhanced growth 7 days post-spraying when compared to the surfactant-only control; the growth of corn was greatest in plants that were sprayed with a combination of 120 mg/liter GA₃ and 10,000 mg/liter GB wherein plant height was increased by 14.2% when compared to the surfactant-only control. Interestingly, the plants that exhibited the greatest increase in growth (compared to control plants) at 13 days post-spraying were treated with a combination of 120 mg/liter GA₃, 9 mg/liter (9-ABA and 10,000 mg/liter GB. This GA₃+(S)-ABA+GB combination provided an additional 2.4% growth benefit compared to the GA₃+(S)-ABA combination and an additional benefit of roughly 1% when compared to GA₃ alone as well as the GA₃+GB combination. At harvest, the GA₃+GB treatment combination as well as the GA₃+(S)-ABA+GB treatment combination numerically increased yield over the control by 3.8 bushels and 1.6 bushels, respectively.

In a corn trial conducted in Arcadia, Iowa, hybrid corn was sown Apr. 30, 2015 and sprayed at V7 with solutions containing a non-ionic surfactant (0.25%, v/v) at 15 gallons of spray volume.

TABLE 13

Corn study conducted in Arcadia, IA in 2015.

| Treatment | Yield (bu/acre) |
|---|---|
| Control | 180.8 |
| GA₃ (120 mg/liter) | 185.8 |
| GA₃ (120 mg/liter) + | 195.3 |

TABLE 13-continued

Corn study conducted in Arcadia, IA in 2015.

| Treatment | Yield (bu/acre) |
|---|---|
| GB (10000 mg/liter) | |
| GA$_3$ (120 mg/liter) + (S)-ABA (9 mg/liter) | 196.9 |
| GA$_3$ (120 mg/liter) + (S)-ABA (9 mg/liter) + GB (10000 mg/liter) | 188.9 |

The data in Table 13 demonstrate that yield increase, resulting from treatment with GA$_3$ alone, is further increased by the addition of glycine betaine. Compared to the control, corn treated with a mixture of GA$_3$ and GB exhibited a 14.5 bushel (8.0%) increase in yield whereas treatment with GA$_3$ alone produced a yield increase of only 5.0 bushels (2.8%). Similarly, the GA$_3$+(S)-ABA+GB treatment mixture increased yield over both the control and GA$_3$ alone by 8.1 bushels (4.5%) and 3.1 bushels (1.71%), respectively.

In a field study conducted in Colby, Kans., corn plants were sprayed with solutions containing a non-ionic surfactant (0.25%, v/v) at 15 gallons of spray solution per acre. Treatments containing the combination of GA$_3$ and GB increased yield above the control as shown in Table 14.

TABLE 14

Corn Study conducted at Colby, KS in 2015.

| Treatment | Yield (bu/acre) |
|---|---|
| Control | 176.9 |
| GA$_3$ (120 mg/liter) | 188.9 |
| GA$_3$ (120 mg/liter) + GB (10000 mg/liter) | 181.8 |
| GA$_3$ (120 mg/liter) + (S)-ABA (9 mg/liter) | 186.3 |
| GA$_3$ (120 mg/liter) + (S)-ABA (9 mg/liter) + GB (10000 mg/liter) | 192.6 |

The results observed for the studies in Table 13 and Table 14 differed; while the GA$_3$+GB treatment mixture produced a greater yield increase than the GA$_3$+(S)-ABA+GB treatment mixture in Table 13, the opposite was observed in Table 14. Respectively, a 4.9 bushel (2.77%) and a surprising 15.7 bushel (8.88%) yield increase over the control was observed in Table 13 for GA$_3$+GB and GA$_3$+(S)-ABA+GB treatment mixtures. This contrast in response between the two studies could be due to the difference in study location as well as the difference in plant growth stage when treatments were applied. Although the data in Table 13 and Table 14 differ in regard to GA$_3$+GB increasing yield over GA$_3$ alone, overall, the addition of Glycine betaine to GA$_3$ and GA$_3$+(S)-ABA improved corn productivity in terms of yield by roughly 3-9% when compared to the control for both studies.

The invention claimed is:

1. A method of increasing growth of a corn plant comprising applying an effective amount of a composition comprising a mixture of from about 30 to about 240 milligrams per liter of GA$_3$ or GA$_4$ and from about 1,000 to 10,000 milligrams per liter of glycine betaine to the corn plant.

2. The method of claim 1, wherein the mixture is applied to the corn plant from corn growth stage period V2 to V6.

3. The method of claim 1 wherein the corn plant is subjected to an abiotic stress selected from the group consisting of cold stress, nutrient stress, drought stress and a combination thereof.

4. The method of claim 1, wherein the GA$_3$ or GA$_4$ is applied at a rate of about 6 to about 21 grams per hectare.

5. The method of claim 4, wherein the GA$_3$ or GA$_4$ is applied at a rate of about 12 to about 20 grams per hectare.

6. The method of claim 1, wherein glycine betaine is applied at a rate of about 840 to about 2,000 grams per hectare.

7. The method of claim 6, wherein glycine betaine is applied at a rate of about 1,000 to about 1,600 grams per hectare.

8. The method of claim 1, wherein the application of the mixture increases corn yield.

9. The method of claim 1, wherein the composition further comprises from about 8 to about 9 milligrams per liter of (S)-(+)-abscisic acid.

10. The method of claim 1, wherein the composition further comprises a non-ionic surface-active agent.

11. The method of claim 10, wherein the non-ionic surface active-agent is at a concentration of about 0.01% to about 0.05% v/v, wherein v/v denotes volume of the entire composition.

12. A method of increasing growth of a corn plant comprising applying an effective amount of a composition comprising a mixture of from about 60 to about 120 milligrams per liter of GA$_3$ or GA$_4$ and from about 1,000 to about 10,000 milligrams per liter of glycine betaine to the corn plant.

13. The method of claim 12, wherein the GA$_3$ or GA$_4$ is applied at a rate of about 16.8 grams per hectare.

14. The method of claim 12, wherein the glycine betaine is applied at a rate of about 1,400 grams per hectare.

15. A composition comprising a mixture of from about 30 to about 240 milligrams per liter of GA$_3$ or GA$_4$ and from about 1,000 to 10,000 milligrams per liter of glycine betaine.

16. A composition of claim 15, wherein the composition further comprises from about 8 to about 9 milligrams per liter of (S)-(+)-abscisic acid.

* * * * *